(12) United States Patent
Pirrotte et al.

(10) Patent No.: US 11,587,644 B2
(45) Date of Patent: Feb. 21, 2023

(54) METHODS OF PROFILING MASS SPECTRAL DATA USING NEURAL NETWORKS

(71) Applicant: THE TRANSLATIONAL GENOMICS RESEARCH INSTITUTE, Phoenix, AZ (US)

(72) Inventors: Patrick Pirrotte, Phoenix, AZ (US); Gil Speyer, Phoenix, AZ (US); Ritin Sharma, Phoenix, AZ (US); Krystine Garcia-Mansfield, Phoenix, AZ (US)

(73) Assignee: The Translational Genomics Research Institute, Phoenix, AZ (US)

( * ) Notice: Subject to any disclaimer, the term of this patent is extended or adjusted under 35 U.S.C. 154(b) by 1057 days.

(21) Appl. No.: 16/049,651

(22) Filed: Jul. 30, 2018

(65) Prior Publication Data
US 2019/0034586 A1  Jan. 31, 2019

Related U.S. Application Data

(60) Provisional application No. 62/538,627, filed on Jul. 28, 2017.

(51) Int. Cl.
*G06N 3/04* (2006.01)
*G16B 40/20* (2019.01)
(Continued)

(52) U.S. Cl.
CPC ........... *G16B 40/20* (2019.02); *G06N 3/0454* (2013.01); *G06N 3/08* (2013.01); *G16B 15/20* (2019.02); *G16B 40/10* (2019.02); *G06N 3/04* (2013.01)

(58) Field of Classification Search
CPC ........ G16B 40/00; G16B 40/10; G16B 40/20; G16B 15/20; G06N 3/04; G06N 3/08; G06N 3/0454
See application file for complete search history.

(56) References Cited

U.S. PATENT DOCUMENTS 9,373,059 B1   6/2016  Heifets et al.
2006/0249668 A1*  11/2006  Goldberg ............. G06K 9/0053
                                                        250/281

(Continued)

OTHER PUBLICATIONS

Baczek, Tomasz et al.; Artificial Neural Network Analysis for Evaluation of Peptide MS/MS Spectra in Proteomics; American Chemical Society; Anal. Chem. 2004, 76, 1726-1732. (Year: 2004).*

(Continued)

*Primary Examiner* — Ying Yu Chen

(57) ABSTRACT

Methods are provided to classify and identify features in mass spectral data using neural network algorithms. A convolutional neural network (CNN) was trained to identify amino acids from an unknown protein sample. The CNN was trained using known peptide sequences to predict amino acid presence, diversity, and frequency, peptide length, subsequences of amino acids classified by features include aliphatic/aromatic, hydrophobic/hydrophilic, positive/negative charge, and combinations thereof. Mass spectra data of a sample unknown to the trained CNN was discretized into a one-dimensional vector and input into the CNN. The CNN models can potentially be integrated to determine the complete peptide sequence from a spectrum, thereby improving the yield of identifiable protein sequences from mass spec analysis.

12 Claims, 17 Drawing Sheets

(51) Int. Cl.
  *G06N 3/08* (2023.01)
  *G16B 40/10* (2019.01)
  *G16B 15/20* (2019.01)

(56) References Cited

U.S. PATENT DOCUMENTS

| | | | |
|---|---|---|---|
| 2008/0108568 | A1 | 5/2008 | Stephan et al. |
| 2017/0329892 | A1* | 11/2017 | Fan ................. G16B 50/30 |
| 2019/0018019 | A1* | 1/2019 | Shan ................. G16B 40/00 |
| 2019/0147983 | A1* | 5/2019 | Shan ............. G01N 33/6848 702/20 |
| 2020/0326348 | A1* | 10/2020 | Qiao ................. G16B 20/00 |

OTHER PUBLICATIONS

Arnold, Randy J. et al.; A Machine Learning Approach to Predicting Peptide Fragmentation Spectra; Pacific Symposium on Biocomputing 11:219-230(2006). (Year: 2006).*

Scherbart, Alexandra et al.; Neural Network Approach for Mass Spectrometry Prediction by Peptide Prototyping; Springer-Verlag Berlin Heidelberg 2007; ICANN 2007, Part II, LNCS 4669, pp. 90-99, 2007. (Year: 2007).*

Li, Sujun et al.; On the Accuracy and Limits of Peptide Fragmentation Spectrum Prediction; ACS Publications; 2010; pp. 790-796. (Year: 2010).*

Ma, Bin; Novor: Real-Time Peptide de Novo Sequencing Software; J. Am. Soc. Mass Spectrom. (2015) 26:1885-1894. (Year: 2015).*

Zhou, Xie-Xuan et al.; pDeep: Predicting MS/MS Spectra of Peptides with Deep Learning; ACS Publications; 2017; Anal. Chem. 2017, 89, 12690-12697. (Year: 2017).*

Lim, Jing et al.; Chemical Structure Elucidation from Mass Spectrometry by Matching Substructures; 2nd NIPS Workshop on Machine Learning for Molecules and Materials (MLMM 2018), Montreal, Canada; pp. 1-10. (Year: 2018).*

Schoenholz, Samuel S. et al.; Peptide-Spectra Matching from Weak Supervision; 2018; pp. 1-19. (Year: 2018).*

Zeng, Wen-Feng et al.; MS/MS Spectrum Prediction for Modified Peptides Using pDeep2 Trained by Transfer Learning; ACS Publications; 2019; Anal. Chem. 2019, 91, 9724-9731. (Year: 2019).*

Lin, Yang-Ming et al.; MS2CNN: predicting MS/MS spectrum based on protein sequence using deep convolutional neural networks; BMC; 2019; BMC Genomics 2019, 20(Suppl 9):906. (Year: 2019).*

Tran et al., "De novo peptide sequencing by deep learning", Jul. 18, 2017, Biophysics and Computational Biology 114 (31), pp. 8247-8252. (Year: 2017).*

Torng et al., "3D deep convolutional neural networks for amino acid environment similarity analysis", Jun. 14, 2017, BMC Bioinformatics (2017) 18:302, pp. 1-23. (Year: 2017).*

Craig et al., "Using Annotated Peptide Mass Spectrum Libraries for Protein Identification", Published on Web Jul. 14, 2006, Journal of Proteome Research 2006, 5, pp. 1843-1849. (Year: 2006).*

Xiong, X. C., et al. Artificial Neural Networks for Classification and Identification of Data of Biological Tissue Obtained by Mass-Spectrometry Imaging. Chin J Anal Chem 2012; 40(1):43-49.

Scherbart, A., et al. Neural Network Approach for Mass Spectrometry Prediction by Peptide Prototyping. Artificial Neural Networks—ICANN 2007. ICANN 2007. Lecture Notes in Computer Science, vol. 4669. Springer, Berlin, Heidelberg; ISBN 978-3-540-74693-5; Abstract only.

Tran, N. H., et al. Protein identification with deep learning: from abc to xyz. 2017; arXiv:/1710.02765.

Tran, N. H., et al. De novo peptide sequencing by deep learning. PNAS 2017; 114(31):8247-8252.

Ma, B., et al. De Novo Sequencing and Homology Searching. Mol Cell Proteomics 2012; 11(2):O111.014902.

Zeiler, M. D., et al. Visualizing and Understanding Convolutional Networks. Computer Vision—ECCV 2014. ECCV 2014. Lecture Notes in Computer Science, vol. 8689. Springer, Cham; ISBN 978-3-319-10589-5.

* cited by examiner

Combined Model Method

[ 0, 0, 0, 0, 0.042052, 0, 0, 0, .0092..., 0.038616 ] [ 1, 0, 1, ..., 1]

One classifier for all 20 AA's

[Y, W, V, U, T, S, R, Q, P, O, N, M, L, K, I, H, G, F, E, D, C, A]

[1, 0, 1, 0, 0, 1, 1, 0, 0, 0, 1, 0, 1, 0, 0, 0, 1, 0, 0, 0, 0, 1]

- $2^{20}$ (1,048,576) possible outputs per model 1 model

FIG. 7

RQIKIWFQNRRMKWKK

Ends with K 18 different subsequences

1) +++
2) +00 and 00+
3) +-- and --+
4) ++0 and 0++
5) +0- and -0+
6) +-+
7) ++- and -++
8) +0+
9) +-0 and 0-+
10) 000
11) 00- and -00
12) 0-- and --0
13) 0-0
14) 0+0
15) ---
16) -0-
17) -+-
18) 0+- and -+0

| | | |
|---|---|---|
| Hydrophobic | Φ | V, I, L, F, W, Y, M |
| Aromatic | Ω | F, W, Y, H |
| Aliphatic (non-aromatic) | Ψ | V, I, L, M |
| Hydrophilic | ζ | S, T, H, N, Q, E, D, K, R |
| Positively charged | + | K, R, H |
| Negatively charged | - | D, E |

FIG. 10

METHODS OF PROFILING MASS SPECTRAL DATA USING NEURAL NETWORKS

CROSS-REFERENCE TO RELATED APPLICATIONS

This application claims the benefit of U.S. Provisional Patent Application No. 62/538,627, filed on Jul. 28, 2017, the contents of which is incorporated herein by reference in its entirety.

FIELD

The present invention relates to the field of identification and profiling of molecules, and more specifically, to convolutional neural network algorithms used to classify and identify features in mass spectral data.

BACKGROUND

Mass spectrometry is used, for example, in protein profiling. De novo sequencing and sequencing matching using a database are current methods for identification of proteins. In database matching, a theoretical sequence is needed in order to match what is being measured or observed. Sequencing databases are primarily comprised of canonical sequence data. A protein mutation, for example caused by a DNA mutation, would not be found in canonical data. In the study of cancer, mutations are ubiquitous. Current methods of database matching are unable to draw conclusions as to whether there is a mutation in the sample being matched. If the sequence is not already in a database, the search engine will not find a match in the database. Post translational modifications (PTMs), for example phosphorylation, may alter the size, shape, weight and/or function of the protein. There are many possible mutations and PTMs for a given peptide or protein. Using conventional methods, search engines and databases are limited in ability to efficiently search for, recognize, and match mutations and PTMs. This is because the computational search space is multiplied by the potential mutations and PTMs, and is too large to be efficiently searched.

Thus, current database methods are unable to recognize proteins having unknown (not previously sequenced) mutations, chemical variations, PTMs, etc. On average, 80% of spectra in a proteomics dataset are not matched in a database. Thus, conventional mass spectra analysis methods only retain approximately 20% of spectra from a sample.

BRIEF DESCRIPTION OF THE DRAWINGS

FIG. 7 illustrates a CNN employing an combined model method for identifying 20 amino acids;

FIG. 10 illustrates a CNN employing a subsequence method;

SUMMARY

Figure 1A:
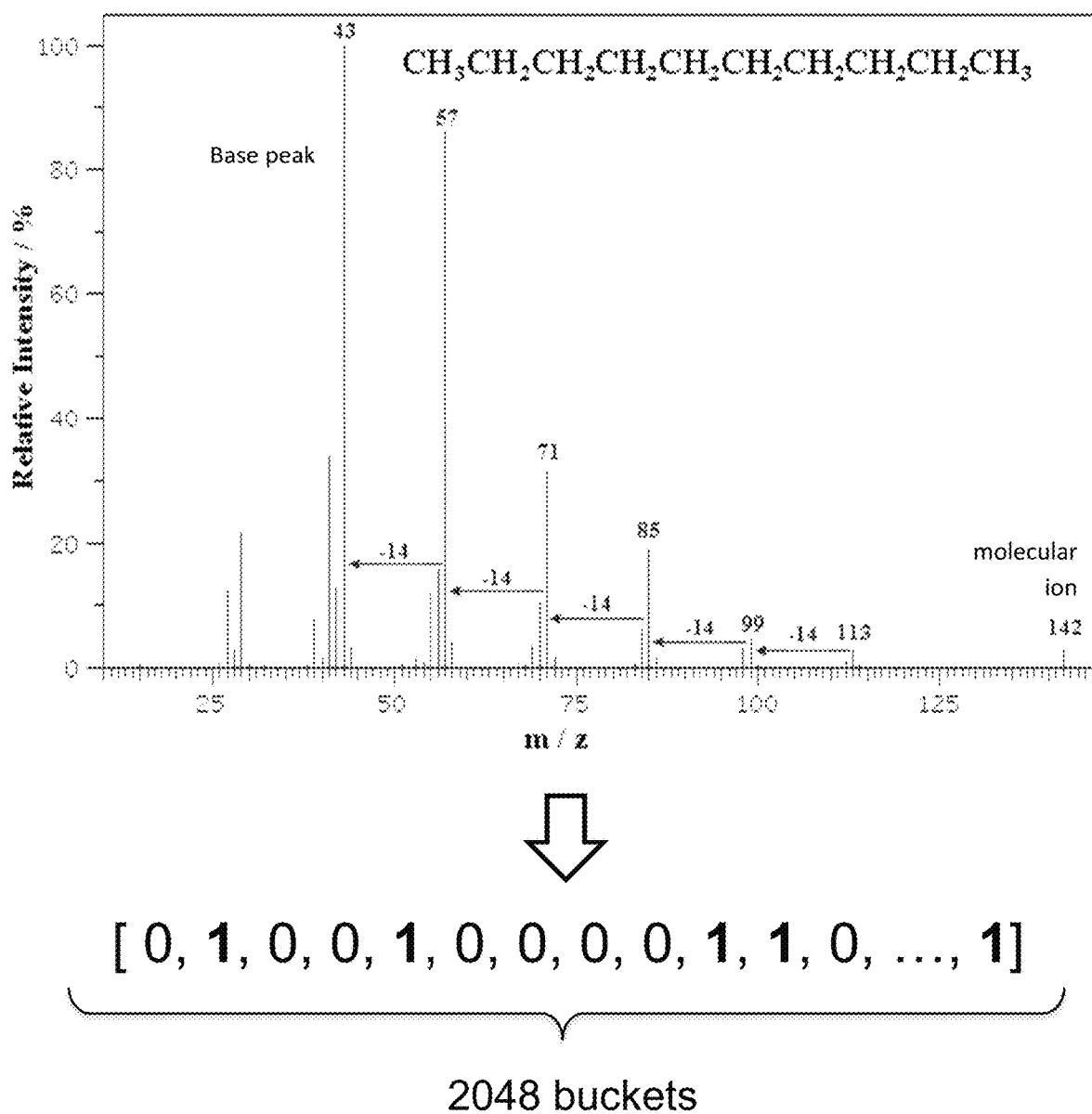
FIGS. 1A and 1B illustrate the mass spectra (mass-to-charge ratio) of a protein and methods of discretizing the spectra data.

A need exists for high throughput, highly sensitive mass-spectrometry analysis of molecules, including proteins. In the present disclosure, various methods and algorithms are employed to achieve identification of molecules (e.g., proteins, metabolites, or small molecules), from mass spectral data, i.e. from tandem mass spectrometry. The methods and algorithms may be applied to confirm the identity of known (spectral-matched) molecules and to identify or further characterize unknown and/or unmatched spectra such as peptides, cyclic peptides, metabolites, non-canonical amino acids, known and unknown post-translational modifications, glycans, lipids, fusion peptides, or other variants not found in canonical databases.

In one embodiment, a method of identifying features in mass spectral data is provided. The method may comprise the steps of inputting a first mass spectrum matched to an amino acid sequence into a convolutional neural network, obtaining from a mass spectrometer a second mass spectrum of a protein sample having an unknown amino acid sequence, discretizing the second mass spectrum into a weighted vector, inputting the weighted vector into the convolutional neural network, and determining, by the convolutional neural network, a predicted amino acid sequence corresponding to the second mass spectrum.

The method may comprise the steps of inputting a mass spectra from a known protein sample and a known sequence into a convolutional neural network, obtaining a mass spectra of an unknown protein sample, inputting the mass spectra of the unknown protein sample into the convolutional neural network, and determining, by the convolutional neural network, a presence or absence of an amino acid in the unknown protein sample.

The foregoing features and elements may be combined in various combinations without exclusivity, unless expressly indicated otherwise. These features and elements as well as the operation thereof will become more apparent in light of the following description. It should be understood, however, the following description is intended to be exemplary in nature and non-limiting.

DETAILED DESCRIPTION

Systems and methods are provided herein for identifying and characterizing proteins, peptides and/or other small molecules from mass spectral data. In the detailed description herein, references to "various embodiments", "one embodiment", "an embodiment", "an example embodiment", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described. After reading the description, it will be apparent to one skilled in the relevant art(s) how to implement the disclosure in alternative embodiments.

As used herein, the terms "comprises", comprising", or any other variation thereof, are intended to cover a non-exclusive inclusion, such that a process, method, article, or apparatus that comprises a list of elements does not include only those elements but may include other elements not expressly listed or inherent to such process, method, article, or apparatus. It is to be understood that unless specifically stated otherwise, references to "a," "an," and/or "the" may include one or more than one and that reference to an item in the singular may also include the item in the plural. Reference to an element by the indefinite article "a," "an" and/or "the" does not exclude the possibility that more than one of the elements are present, unless the context clearly requires that there is one and only one of the elements. As used herein, the term "comprise," and conjugations or any other variation thereof, are used in its non-limiting sense to mean that items following the word are included, but items not specifically mentioned are not excluded.

The present disclosure relates to a deep learning approach to molecule identification and profiling from mass spectral data. Machine learning gives computers the ability to learn, without being explicitly programmed, and to make predictions from data. A neural network involves a mathematical model that maps inputs to outputs through "web-like" connections (weights), and the weights may be iteratively optimized. As disclosed herein, deep learning conducts automatic feature extraction on data from mass spectrometry (i.e, spectra), and enables computation on highly non-linear problems. A convolutional neural network (CNN) uses network layers as detection filters for the presence or absence of specific features, and employs feature learning and classification.

The terms "polypeptide," "peptide," and "protein" are used interchangeably herein to refer to polymers of amino acids of any length. These terms also include proteins that are post-translationally modified through reactions that include glycosylation, acetylation and phosphorylation. The term "at least a portion" of a polypeptide means a portion having the minimal size characteristics of such sequences, or any larger fragment of the full length molecule, up to and including the full length molecule. For example, a portion of a polypeptide may be 4 to 15 amino acids, or may be 4 amino acids, 5 amino acids, 6 amino acids, 7 amino acids, and so on, up to a full length polypeptide. A portion of a polypeptide useful as an epitope may be as short as 4 amino acids. A portion of a polypeptide that performs the function of the full-length polypeptide would generally be longer than 4 amino acids.

The term "amino acid" refers to naturally occurring and synthetic amino acids, as well as amino acid analogs and amino acid mimetics that function in a manner similar to naturally occurring amino acids. Naturally occurring amino acids are those encoded by the genetic code, as well as those amino acids that are later modified. Unnatural amino acids are not encoded by the genetic code and can, but do not necessarily have the same basic structure as a naturally occurring amino acid. "Amino acid analogs" refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs may have modified R groups (e.g., norleucine) or modified peptide backbones, but retain the same basic chemical structure as a naturally occurring amino acid. "Amino acid mimetics" refers to chemical compounds that have a structure that is different from the general chemical structure of an amino acid, but that functions in a manner similar to a naturally occurring amino acid.

Amino acids may be referred to by either the three letter symbols or by the one-letter symbols recommended by the IUPAC, the IUAPC letter code are as follows: G=Glycine; A=Alanine; L=Leucine; M=Methionine; F=Phenylalanine; W=Tryptophan; K=Lysine; Q=Glutamine; E=Glutamic Acid; S=Serine; P=Proline; V=Valine; I=Isoleucine; C=Cysteine; Y=Tyrosine; H=Histidine; R=Arginine; N=Asparagine; D=Aspartic Acid; T=Threonine.

"Variants" applies to both amino acid and nucleic acid sequences. Because of the degeneracy of the genetic code, a large number of functionally identical nucleic acids encode any given protein. For instance, the codons GCA, GCC, GCG and GCU all encode the amino acid alanine. Variants may include individual substitutions, deletions or additions to a nucleic acid, peptide, polypeptide, or protein sequence which alters, adds or deletes a single amino acid or a small percentage of amino acids in the encoded sequence.

As used herein, the term "sample" is used in its broadest sense and can be obtained from any source. A sample may refer to a bodily sample obtained from a subject (e.g., a human). A "sample" may be any cell source from which DNA, including genomic, somatic, and germline DNA, RNA (i.e., any form of RNA), and/or protein may be obtained. A sample can include a "clinical sample", i.e., a sample derived from a subject. Samples may include, but are not limited to, peripheral bodily fluids, which may or may not contain cells, e.g., blood, urine, plasma, and serum. Samples may include, but are not limited to, archival samples with known diagnosis, treatment and/or outcome history. Samples may include, but are not limited to, tissue or fine needle biopsy samples, and/or sections of tissues, such as frozen sections taken for histological purposes. For example, in some forms of cancer, a sample may be obtained from the local site of the tumor and may include tissue adjacent to the tumor. Thus, a sample may contain both tumor and non-tumor cells. The term "sample" may also encompass any material derived by processing the sample. Derived materials can include, but are not limited to, cells (or their progeny) isolated from the biological sample and proteins extracted from the sample. Processing of the biological sample may involve one or more of, filtration, distillation, extraction, concentration, fixation, inactivation of interfering components, addition of reagents, and the like. In various embodiment, mass spectrum data is obtained from a mass spectrometer for a sample, such as a protein sample, having an unknown amino acid sequence. The methods disclosed herein use a CNN to predict the amino acid sequence of the sample based on the mass spectrum data input into the CNN.

The following examples are given for purely illustrative and non-limiting purposes of the present invention.

In order to implement deep learning in protein profiling, a CNN was built based on a set of protein sequences from a known amino acid sequence database, which were used to teach or train the CNN. The disclosed CNN was built using the Keras deep learning library with graphics processing unit (GPU) acceleration. The platforms that may be used for the CNN may include GPU or central processing unit (CPU), CUDA (a parallel computing platform and programming model by NVIDIA), CUDA Deep Neural Network library (cuDNN), Theano library, Keras deep learning library, PyCharm IDE, and the like. The GPU used for the CNN may include one or more processors and one or more tangible, non-transitory memories and be capable of implementing logic. The processor can be a general purpose processor, a digital signal processor (DSP), an application specific integrated circuit (ASIC), a field programmable gate array (FPGA) or other programmable logic device, discrete gate or transistor logic, discrete hardware components, or a combination thereof.

System program or processing instructions may be loaded onto a non-transitory, tangible computer-readable medium having instructions stored thereon that, in response to execution by a controller, cause the controller to perform various operations. The term "non-transitory" is to be understood to remove only propagating transitory signals per se from the claim scope and does not relinquish rights to all standard computer-readable media that are not only propagating transitory signals per se. Stated another way, the meaning of the term "non-transitory computer-readable medium" and "non-transitory computer-readable storage medium" should be construed to exclude only those types of transitory computer-readable media which were found in In Re Nuijten to fall outside the scope of patentable subject matter under 35 U.S.C. § 101.

In mass spectrometry for protein profiling, a protein sample is broken down into its constituent parts, i.e. peptides, using an enzyme, such as trypsin.

FIG. 1A shows tandem mass spectrometry (MS/MS) data (spectra) as a bar graph of the mass (m) per charge (z) of protein fragments (i.e., peptides), shown on the x-axis as m/z, against their relative abundance in the sample, shown on the y-axis as relative intensity as a percentage.

In one embodiment, the mass spectra data for the sample was discretized to a one-dimensional vector, illustrated as [0, 1, 0, 0, 1, 0, 0, 0, 0, 1, 1, 0, . . . , 1]. The one-dimensional vector represents peak data from the mass spectra. The mass/charge (m/z) axis was discretized by dividing the peak data into a number of groups or "buckets." Stated differently, the peak data was analyzed by looking at the abundance in a given segment of m/z. If the abundance peak exceeded a threshold in a segment (or bucket) of m/z, the corresponding position on the vector was assigned a 1, with 1 meaning a peak was present. If a peak was not present for a given segment (or bucket) of m/z or below a threshold, the corresponding position on the vector was assigned a 0, with 0 meaning that no significant peak was present. In the example shown in FIG. 1A, the spectra data was divided into 2,048 segments (or buckets) for evaluating the peak data. The peak data was evaluated in binary manner (peak=1; no peak=0) to create the one-dimensional vector, which represents the peak data for this spectra.

Figure 1B:
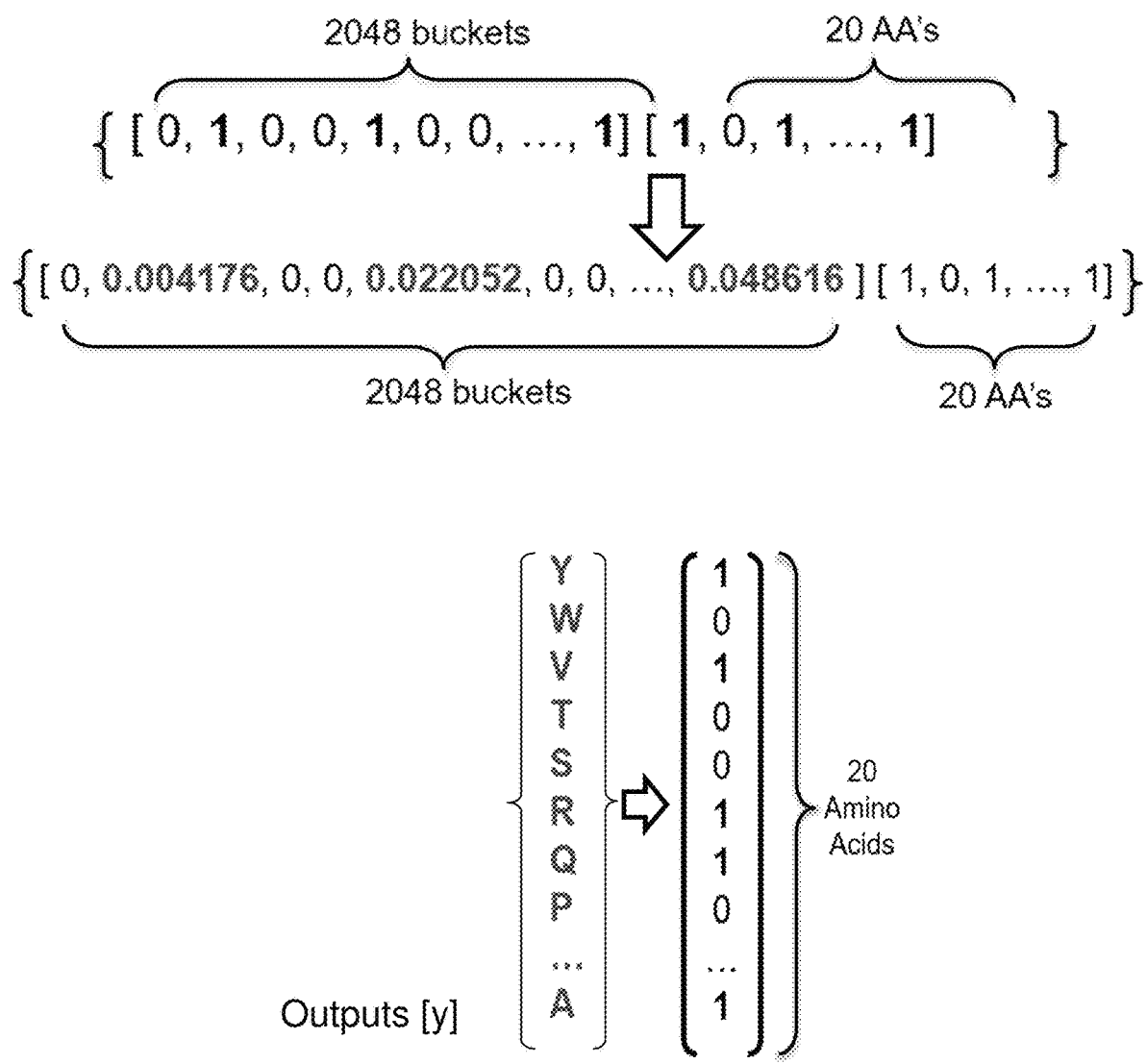

FIG. 1B shows a method of discretizing the spectra by incorporating the peak height into the vector-based analysis. In this embodiment, the mass spectra data for the sample was discretized to a one-dimensional weighted vector, illustrated as [0, 0.004176, 0, 0, 0.022052,00, . . . , 0.048616]. The magnitude of peak height from the spectra was used as an input to create the weighted vector. Rather than creating a binary vector, with a 1 indicating a presence of a peak, the peak magnitude was input into the vector.

Figure 2A:
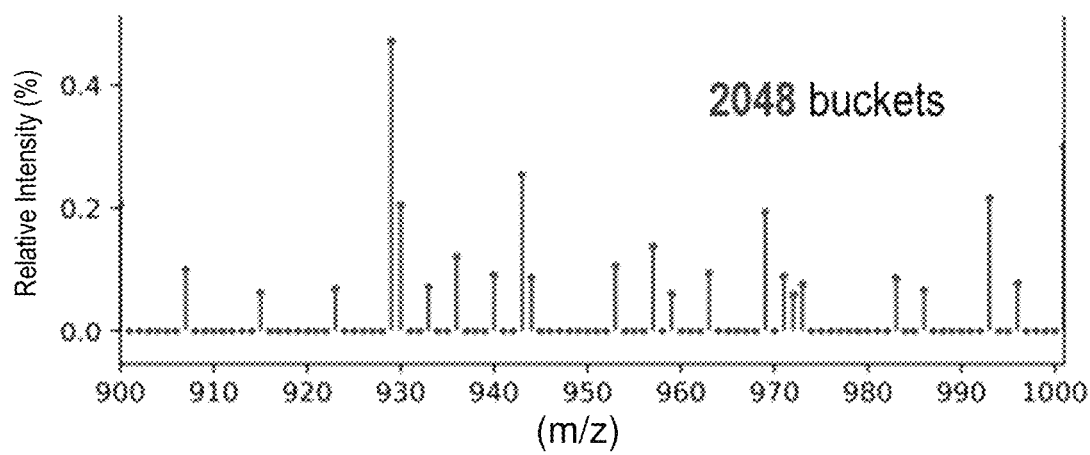
FIGS. 2A-2C illustrate the mass spectra of a sample discretized into various quantities of buckets.
Figure 2B:
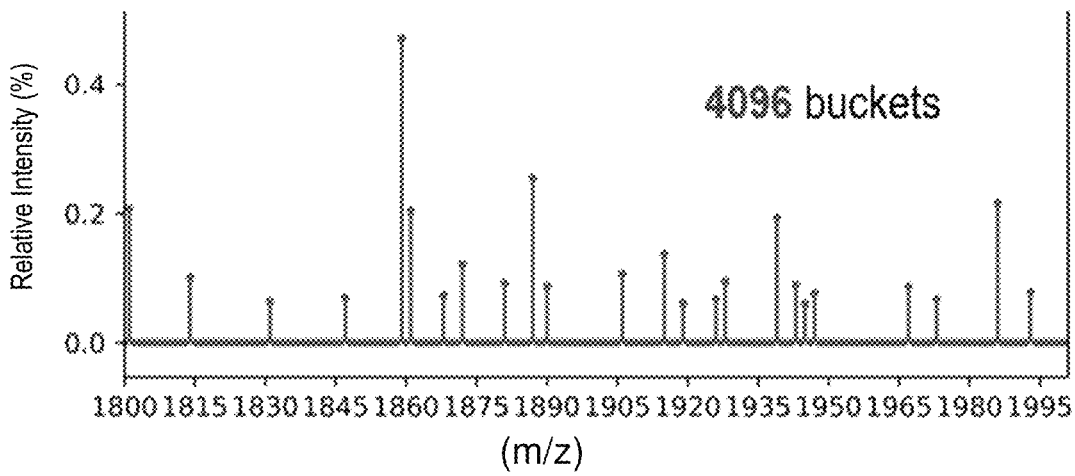
Figure 2C:
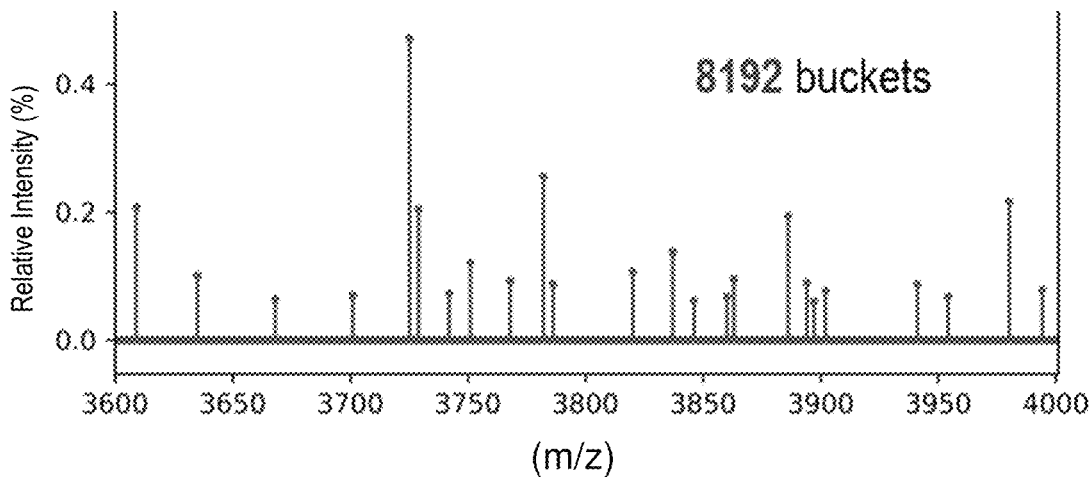

FIGS. 2A-2C illustrate mass spectra data (MS/MS data) that has been discretized into segments, or buckets. In FIGS. 2A-2C, a sample was discretized using three bucket quantities (2,048; 4,096; 8,192). FIGS. 2A-2C shows that discretizing into more buckets results in a greater resolution in the peak data. The peaks represent the presence of peptides at the various weights. The relative distances between peaks provides information about the presence of amino acids in the sample.

Figure 3:
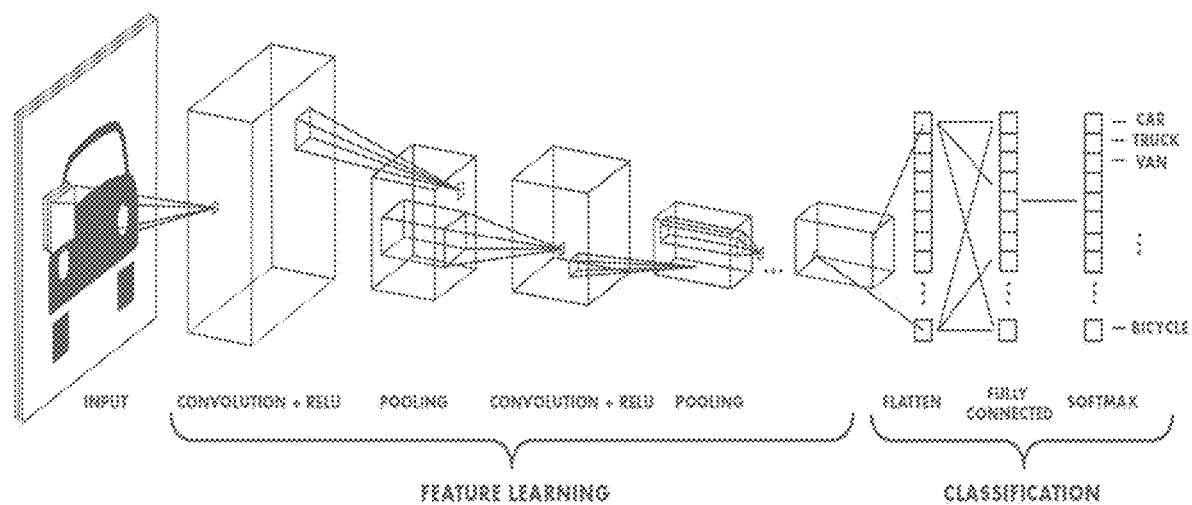
FIG. 3 illustrates a general schematic view of a convolutional neural network (CNN)

Returning to FIGS. 1A and 1B, the spectrum was discretized by identifying the presence of a peak (presence of a peptide at that weight) as a 1, and identifying the absence of a peak as a 0. The presence or absence of a peak was identified for 2,048 different weights ("buckets"). Each input was associated with a labeled output of amino acid data. This data was fed into a convolutional neural network, a feed-forward neural network, that automatically filters spatial features in images or vectors, shown schematically in FIG. 3.

The CNN uses feature learning and classification to identify amino acids in the sample. Convolutional and pooling layers are used to divide the one-dimensional vector into smaller "images." Pooling methods combine multiple images into one image to look for a feature. Based on the features found in the convolution and pooling steps, the CNN classifies (or identifies) the presence or absence of each amino acid.

To train the CNN, protein samples with known spectra (i.e., spectra already matched to a protein) were used to train the CNN to recognize, based on the sequence output, what the input spectra should look like. Stated differently, the CNN was given expected sequence outputs matched to known spectra input, in order to teach the CNN to recognize spectra that the CNN did not know. The CNN was also trained using synthetic spectra, by taking a known sequence and developing a theoretical (synthetic) mass spectra data. In various embodiments, a first portion of a spectra set is used as knowns or controls to teach the CNN, and subsequently, a second portion of the spectra set (unknown to the CNN) is input into the CNN to test the accuracy with which the CNN can identify the presence or absence of an amino acid. The first portion of control spectra may include spectra data (for example, weighted peaks translated into a weighted vector as described above) and may further include amino acid sequences matched to the spectra data. For testing the CNN, the second spectra set may include spectra data (for example, weighted peaks translated into a weighted vector) that had not previously been introduced into the CNN, but that could be verified by the testers using the amino acid sequence matched to that spectra data. The CNN predicted an amino acid sequence for the second spectra set based on the previous training which used the control spectra. The accuracy of the CNN was determined by comparing the CNN-predicted amino acid sequence to the database-matched amino acid sequence for the particular spectra data.

After training the CNN using spectra matched to a protein or peptide sequence, a spectra from an unknown or unmatched protein or peptide is input into the CNN. The CNN processes the input spectra in order to identify the amino acid sequence based on the input spectra and based on what the CNN has been trained on, i.e. based on the information the CNN has learned from the training inputs and outputs, the training spectra and sequences.

Figure 4A:
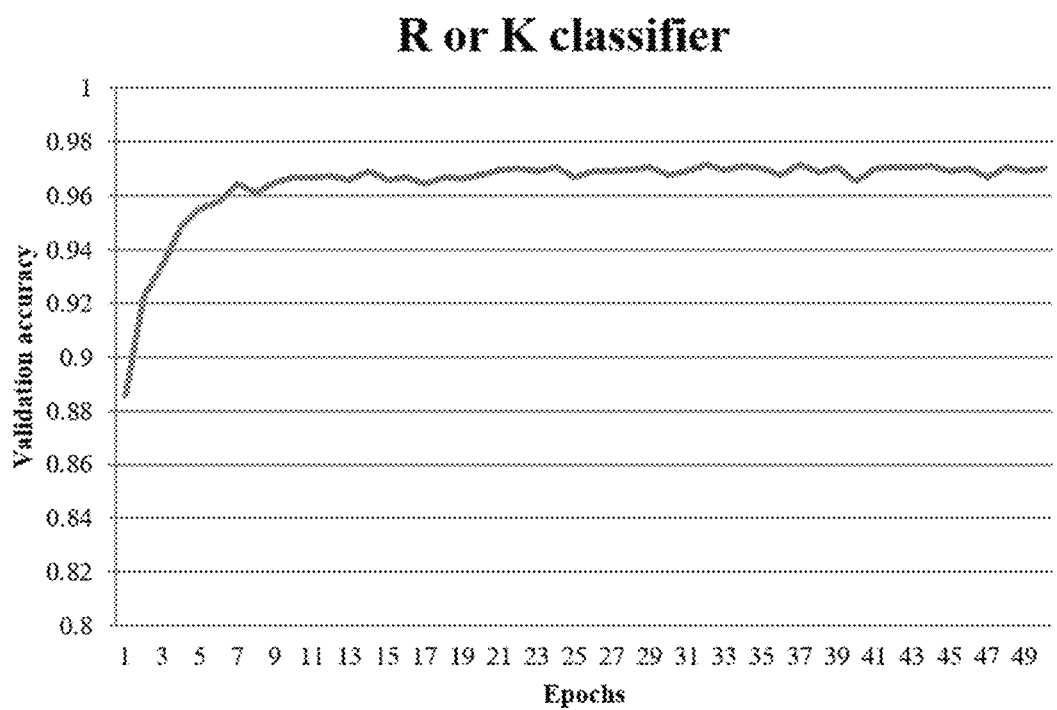
FIGS. 4A and 4B illustrate validation results for an "R or K" amino acid classification CNN algorithm.
Figure 4B:
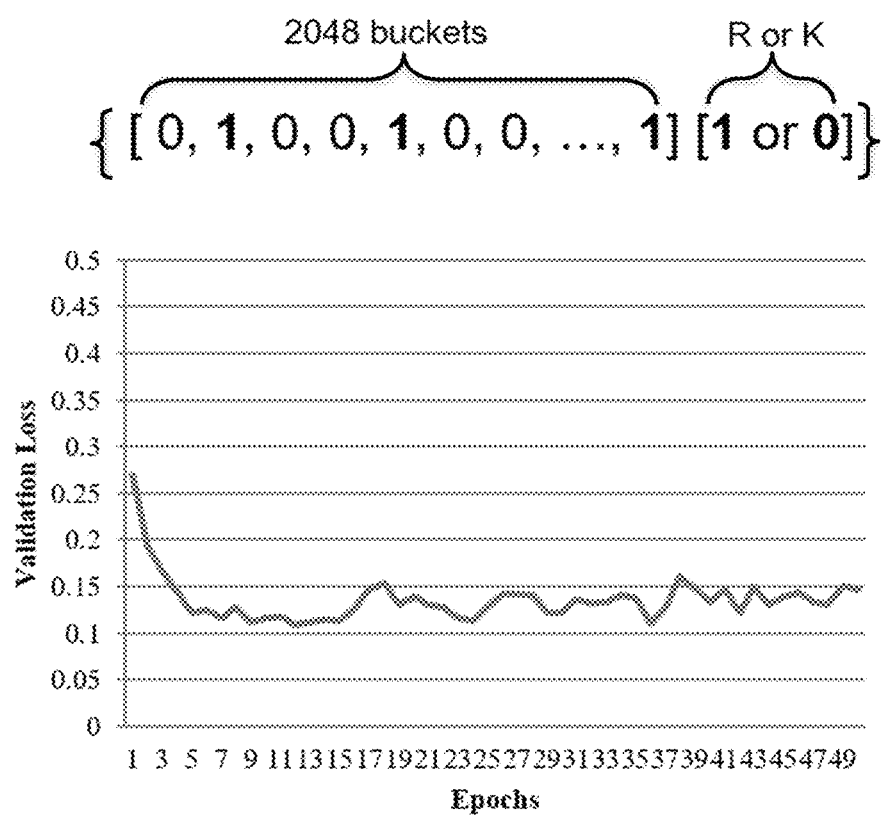

For preliminary validation, a CNN was created to identify spectra with sequences that ended with one of two amino acids, arginine (R) or lysine (K). FIGS. 4A and 4B show results of the "R or K" validation test. Spectra with peptide sequences ending in either an R (arginine) or a K (lysine) amino acid was input into the trained CNN. The spectra were unknown to the CNN prior to the test. The CNN analyzed the spectra and determined whether the peptide sequences ended in an R or a K. The validation accuracy was found to be about 97% (+/−1%) after approximately 10 iterations (epochs). The results also show that the accuracy generally plateaus over some number of iterations, typically less than 20 iterations. The iterations were used to tune the weights of the inputs to improve accuracy over the iterations.

Figure 5:
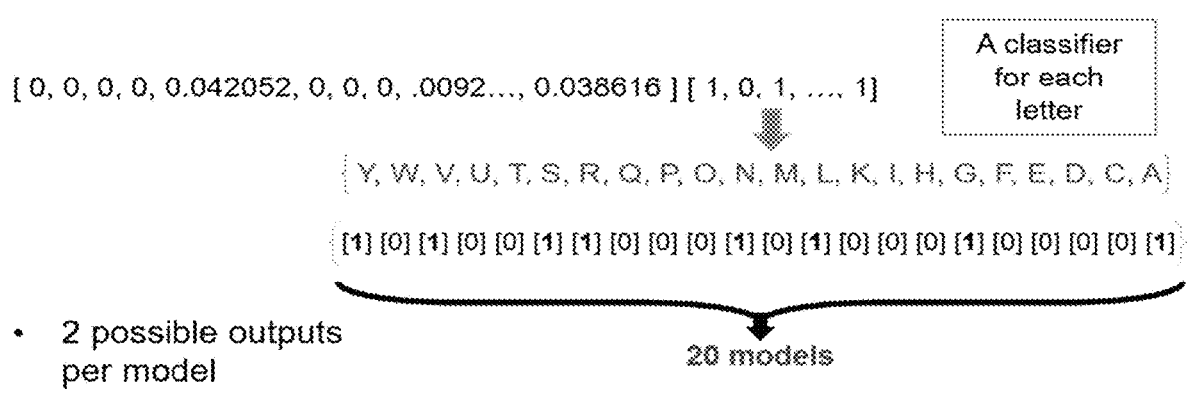
FIG. 5 illustrates a CNN employing an individual model method for identifying 20 amino acids.

FIG. 5 shows a CNN employing an individual model method for identifying a protein or peptide or other molecule comprised of a sequence of amino acids, where each amino acid is one of 20 potential amino acids. The individual model used a classifier for each amino acid (indicated by a letter) of the 20 amino acids. The individual model method created a two-class classifier for each amino acid with a binary output (presence/non-presence of the amino acid). The input data for the CNN were one-dimensional vectors. The input comprised a vector produced from the spectral data, wherein the vector included the weighted peak values where peaks were present in the spectra. The vector further included a zero in the vector at each m/z segment that included no peak. The individual model method reached about 97% accuracy.

Figure 6A:
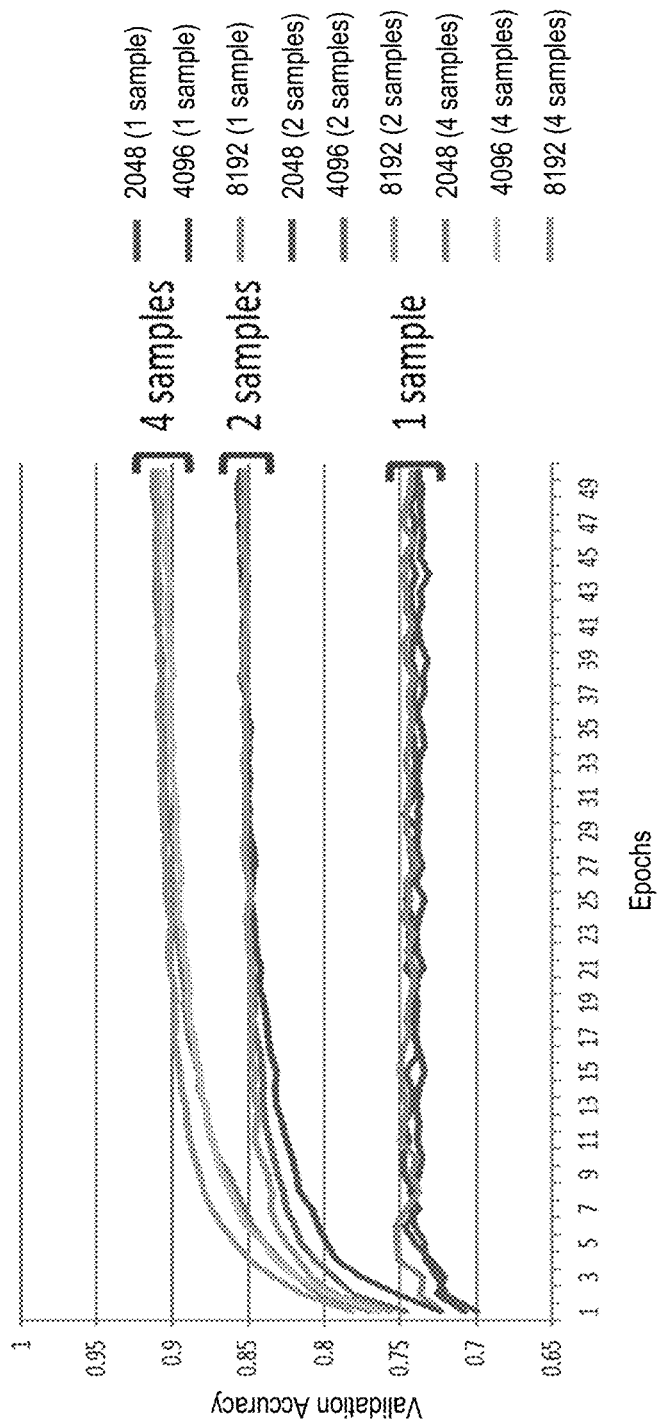
FIGS. 6A and 6B illustrates validation results for an amino acid classification CNN algorithm using various sample quantities and resolution.
Figure 6B:
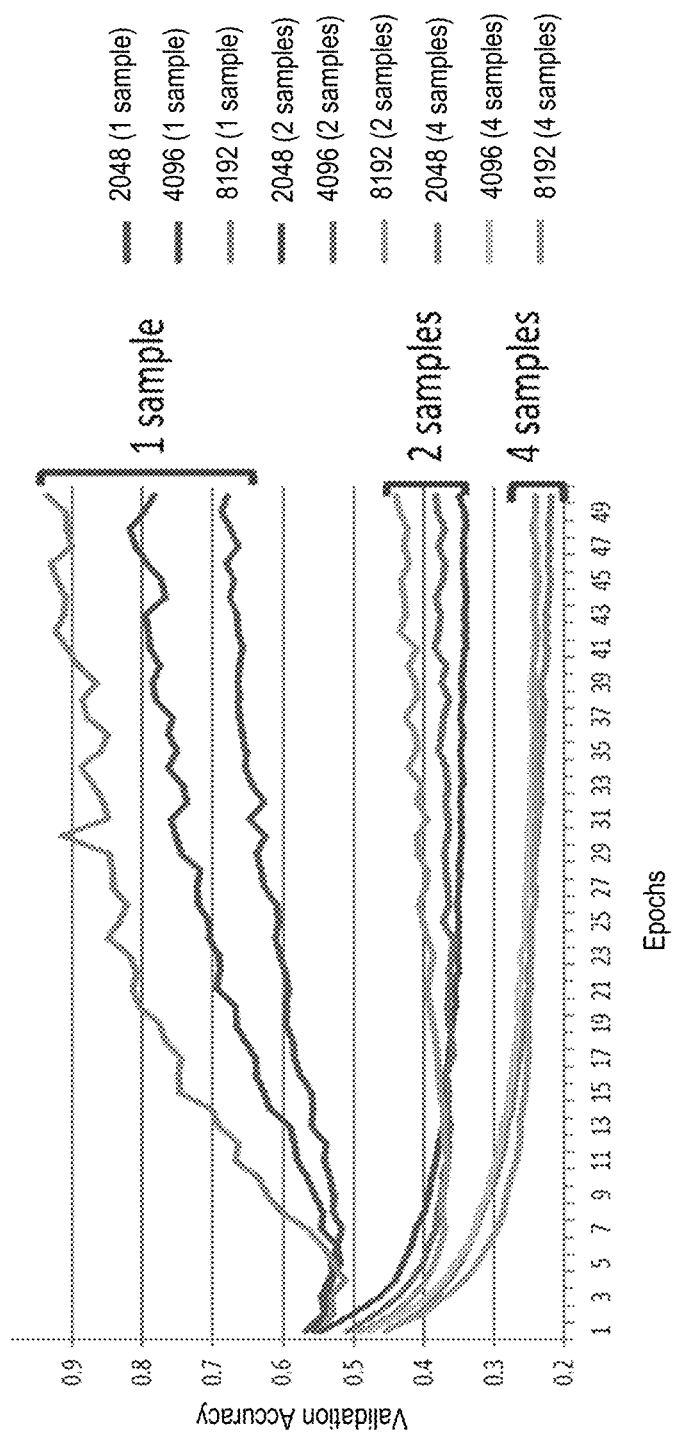

FIGS. 6A and 6B show validation results for an amino acid classification CNN algorithm using various sample quantities and resolution. In this study, 1 sample provided 7,049 spectra, 2 samples provided 13,807 spectra, and 4 samples provided 27,520 spectra, where each spectra corresponds to a protein. A greater number of available spectra allowed the CNN to be trained on a greater quantity of spectra. The spectra were discretized using different resolutions: 2,048 buckets, 4,096 buckets, and 8,192 buckets. The results in FIG. 6A show that an increase in samples resulted in an increase in the validation accuracy from about 75% for 1 sample, to about 85% for 2 samples, and to about 90% for 4 samples.

FIG. 7 shows a CNN employing a combined model method for identifying a protein or peptide or other molecule comprised of a sequence of amino acids, where each amino acid is one of 20 potential amino acids. The combined model used one classifier for all 20 amino acids. The combined model method incorporated one $2^{\wedge}20$-class amino acid classifier with a categorical output (outputs a specific class). The combined model method reached about 93% accuracy.

Figure 8:
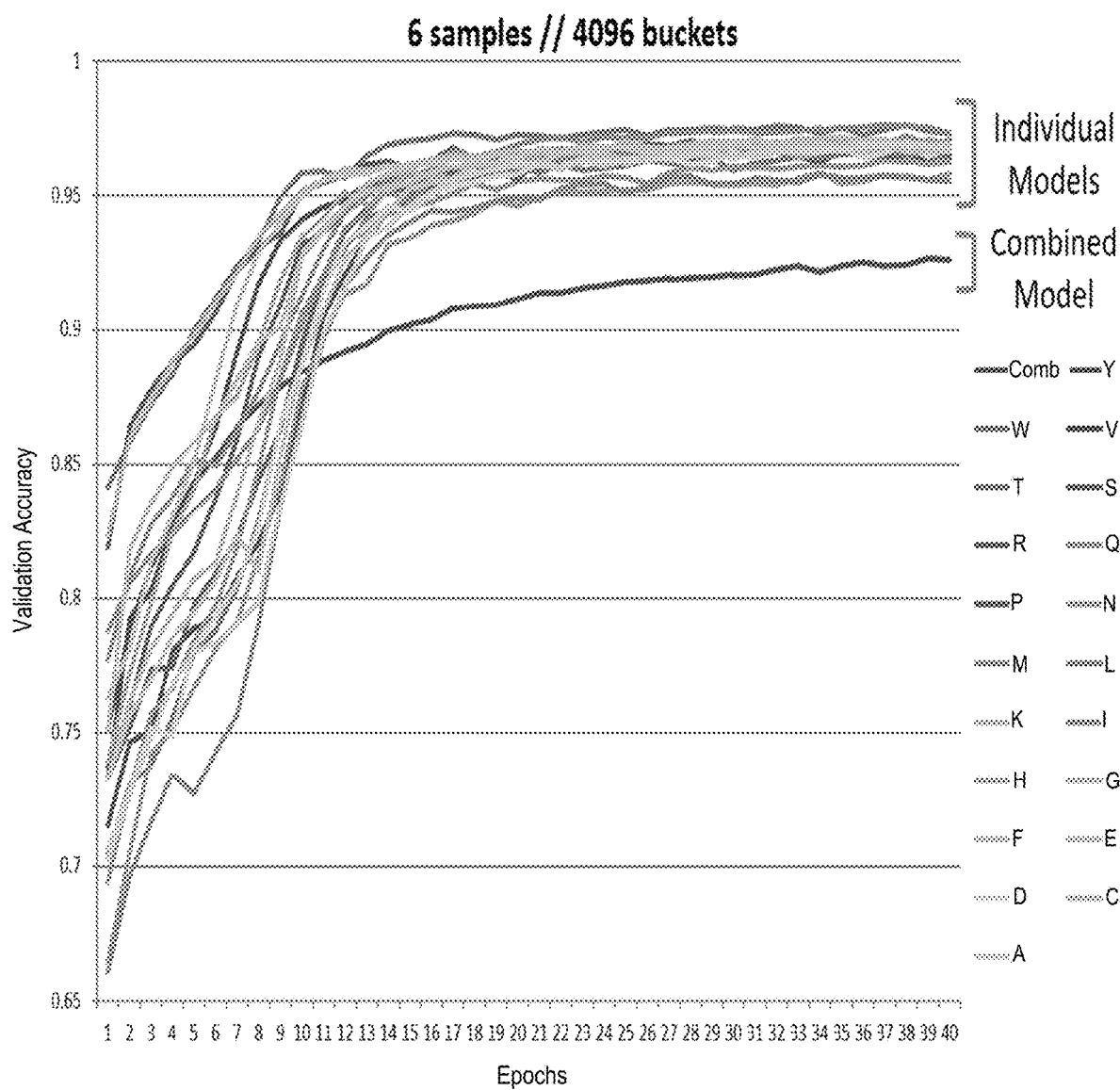
FIG. 8 illustrates validation results for an amino acid classification CNN algorithm using the individual model method and the combined model method.

FIG. 8 shows validation results for an amino acid classification CNN algorithm using the individual model method and the combined model method. The results show that the accuracy of the individual model method was above 95% for all 20 amino acids. The data shows that the CNN can be trained to recognize the presence or absence of amino acids.

In addition to testing whether the CNN could identify the presence or absence of amino acids, additional models were tested to determine if the CNN could predict the length of a peptide sequence (i.e., the quantity of amino acids in a peptide sequence), the diversity of amino acids in a peptide sequence (i.e., the number of unique amino acids in a peptide sequence), and the frequency of amino acids in a peptide sequence (i.e., the number of a specific amino acid present in a peptide sequence). The validation accuracy of the length, diversity, and frequency models were each about 92%.

Referring to FIG. 10, the CNN was also trained and validated using a subsequence method. For the subsequence method, the known peptide sequences used for training the CNN were pooled into groups of three amino acids. As shown in FIG. 10, a protein or peptide sequence was pooled into multiple groups of three sequential amino acids, wherein the pools may overlap. Subsequences were determined by the amino acid's charge, water affinity, and chemical makeup. Looking at each group of three sequential amino acids, the characteristics of each amino acid in the group were identified. The amino acids were identified and classified by aliphatic, aromatic, hydrophobic, hydrophilic, positive charge, neutral charge, negative charge. For each amino acid, the three features were identified (classified). The groups of three amino acids were then characterized into subsequences based on the classifications. With three amino acids in a group each having three features (aliphatic/aromatic; hydrophobic/hydrophilic; positive/neutral/negative charge), a subsequence was created. Each subsequence is shown in FIG. 10 having nine total features.

Then, the CNN was trained to determine if the subsequences were present or absent (1 or 0). The CNN was also trained to determine a frequency of each subsequence. The CNN was then used to determine not only the presence and frequency of the individual amino acids, but also the presence and frequency of the subsequences.

The presence or absence of each subsequence, the presence or absence of each individual amino acids, the frequency of each subsequence and the frequency of each individual amino acids are used as inputs to the CNN. These inputs can be processed by the CNN using an algorithm to layer and organize the inputs over one or more iterations in order to determine the sequence of the input.

Figure 11:
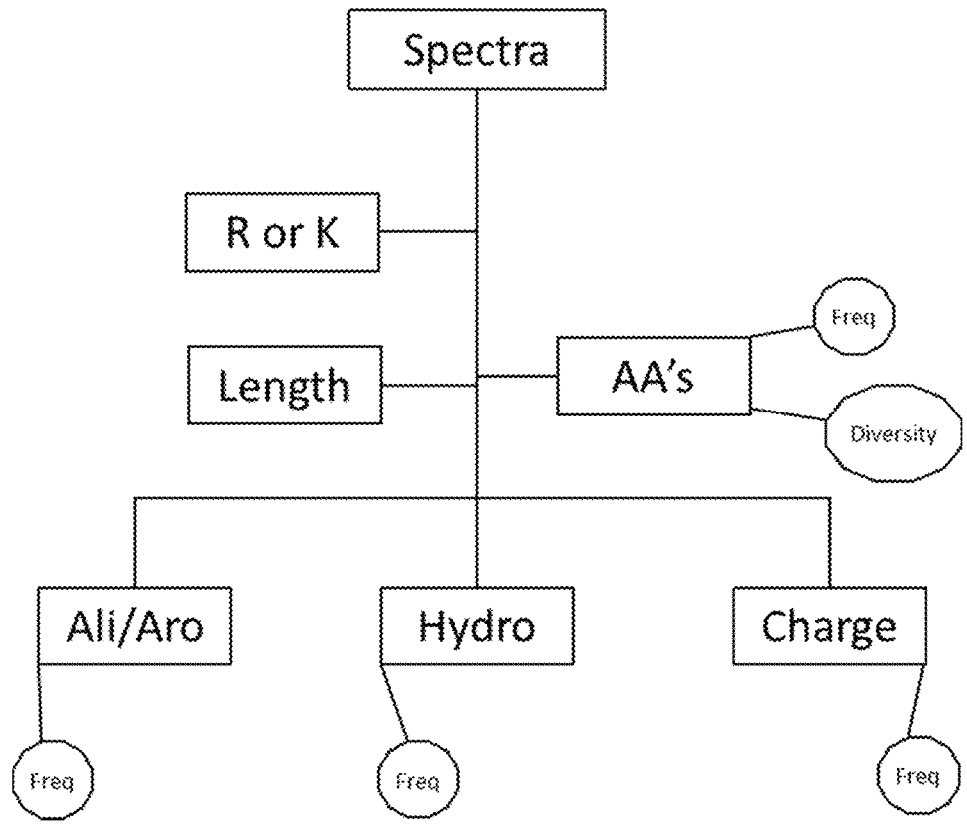
FIG. 11 illustrates various CNN algorithms using the subsequences.

Referring to FIGS. 10 and 11, each subsequence contained three amino acids and each of the three amino acids within the subsequences were classified based on the three features (aliphatic/aromatic; hydrophobic/hydrophilic; positive/neutral/negative charge). For example, hydrophobic amino acids include valine, leucine, isoleucine, methionine, phenylalanine, and tryptophan. For example, aromatic amino acids include phenylalanine, tyrosine and tryptophan. For example, aliphatic amino acids include serine and threonine. For example, basic amino acids include lysine, arginine and histidine. For example, amino acids with carboxylate side-chains include aspartate and glutamate. For example, amino acids with carboxamide side chains include asparagine and glutamine.

After classification based on the three features, 18 unique subsequences were identified. The CNN then determined which amino acids are present based on the three subsequences, and determined the possible amino acid sequences that comprise the unknown peptide. The validation accuracy of the subsequence method reached about 96%.

Figure 9A:
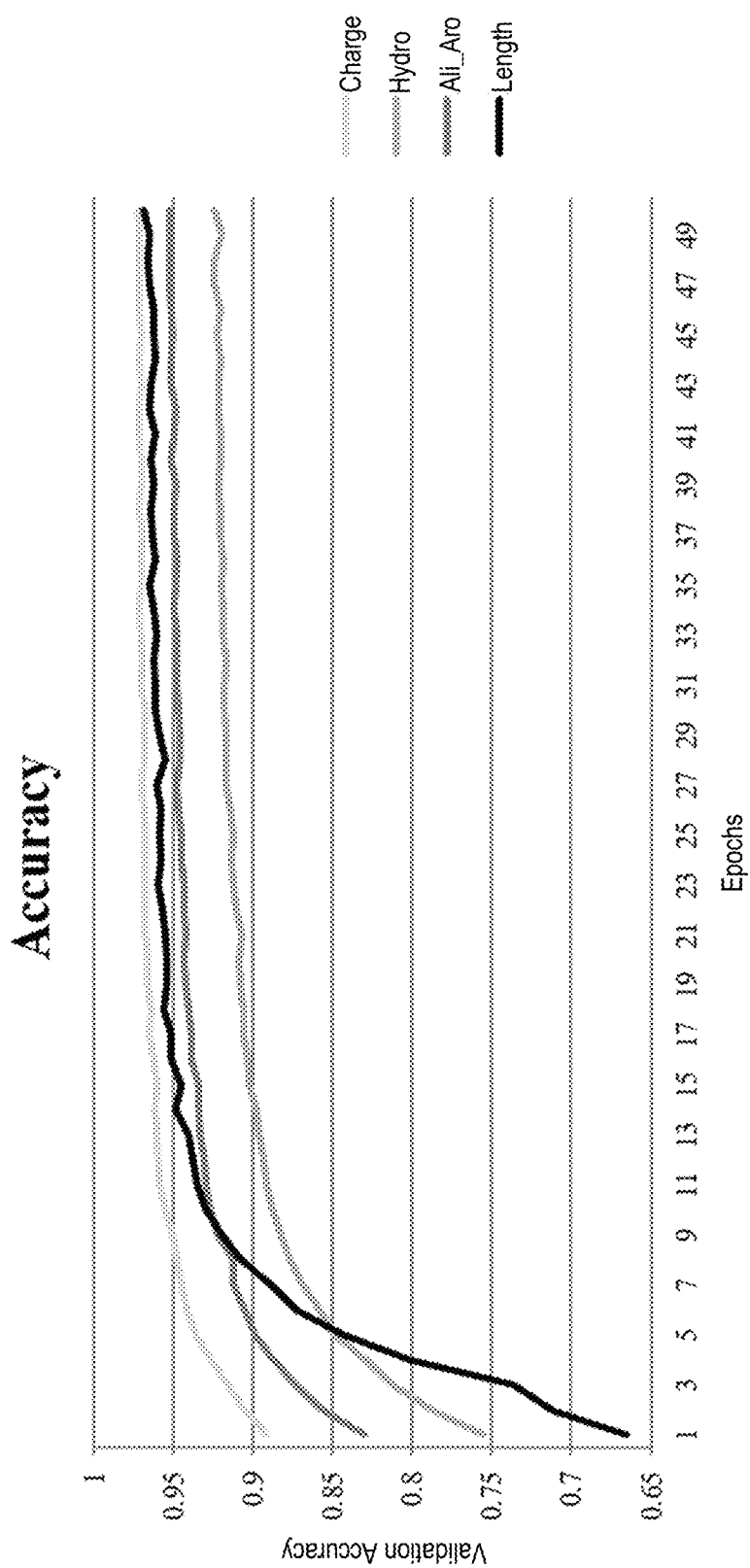
FIGS. 9A and 9B illustrates validation results CNN algorithm in predicting peptide characteristics.
Figure 9B:
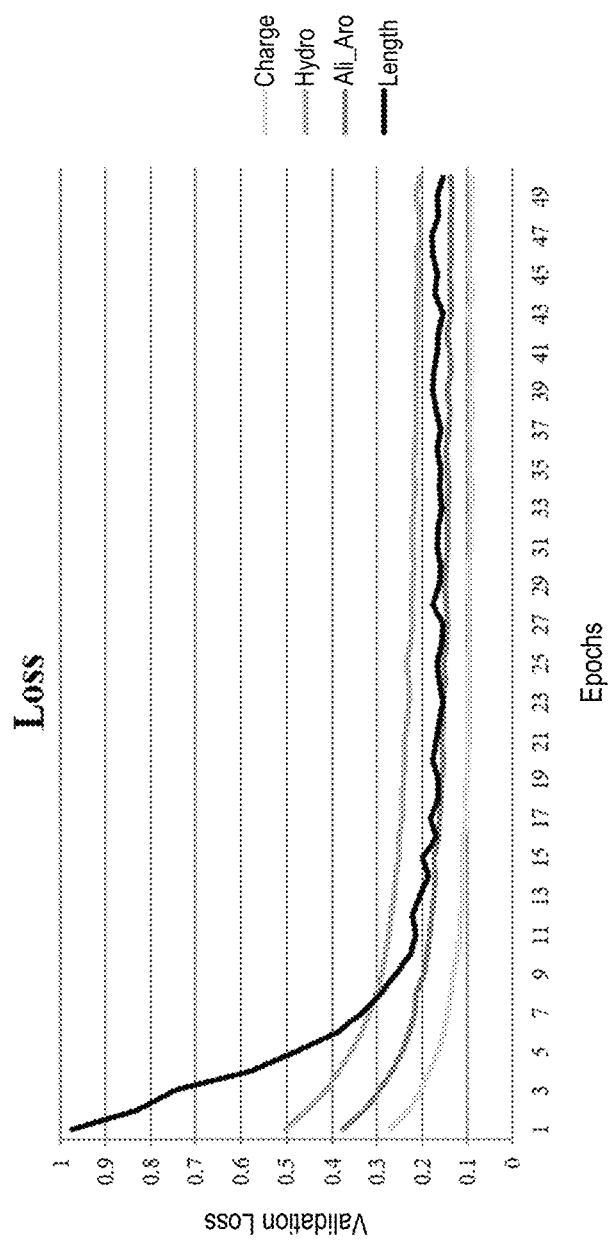

FIGS. 9A and 9B show results of validating the CNN which was trained using the subsequence method. Referring to FIG. 9A, for example, the validation accuracy for the CNN algorithm using the subsequence method for predicting peptide length reached above 95% after approximately 18 iterations (epochs).

Any of these models can be integrated to determine the complete peptide sequence from a spectrum, thereby improving the yield of identifiable protein sequences from mass spec analysis. Further, other features of interest can be selected and used to train the CNN for identification of the features of interest in an unknown sample.

Figure 12A:
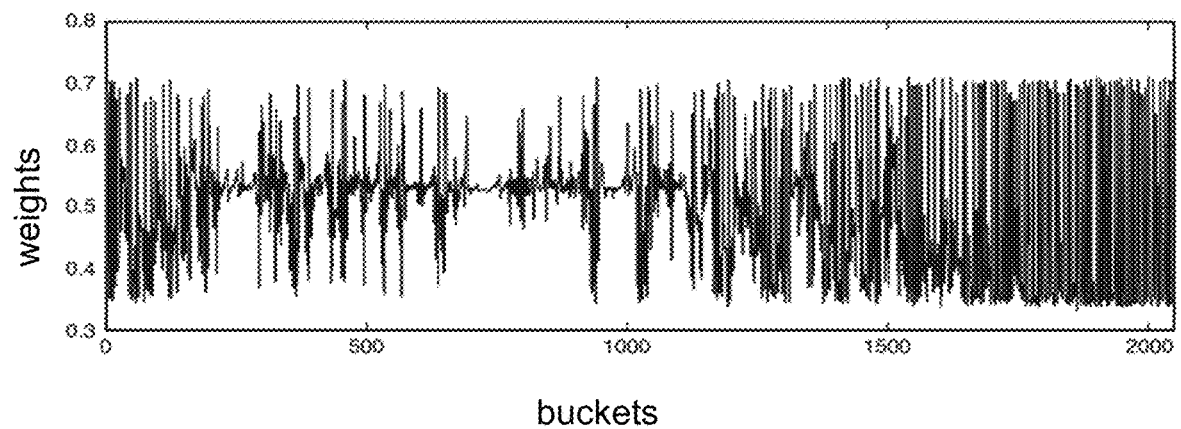
FIGS. 12A-12C illustrate the final layer in an exemplary CNN.
Figure 12B:
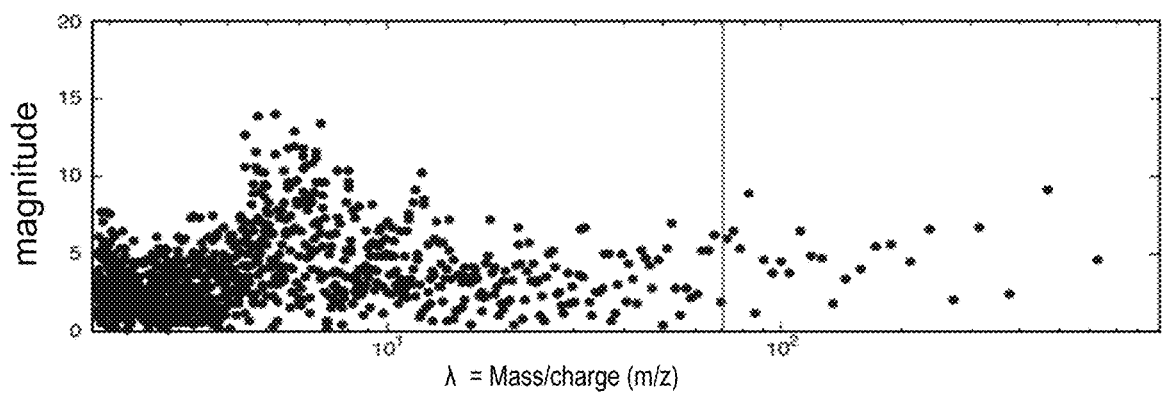
Figure 12C:
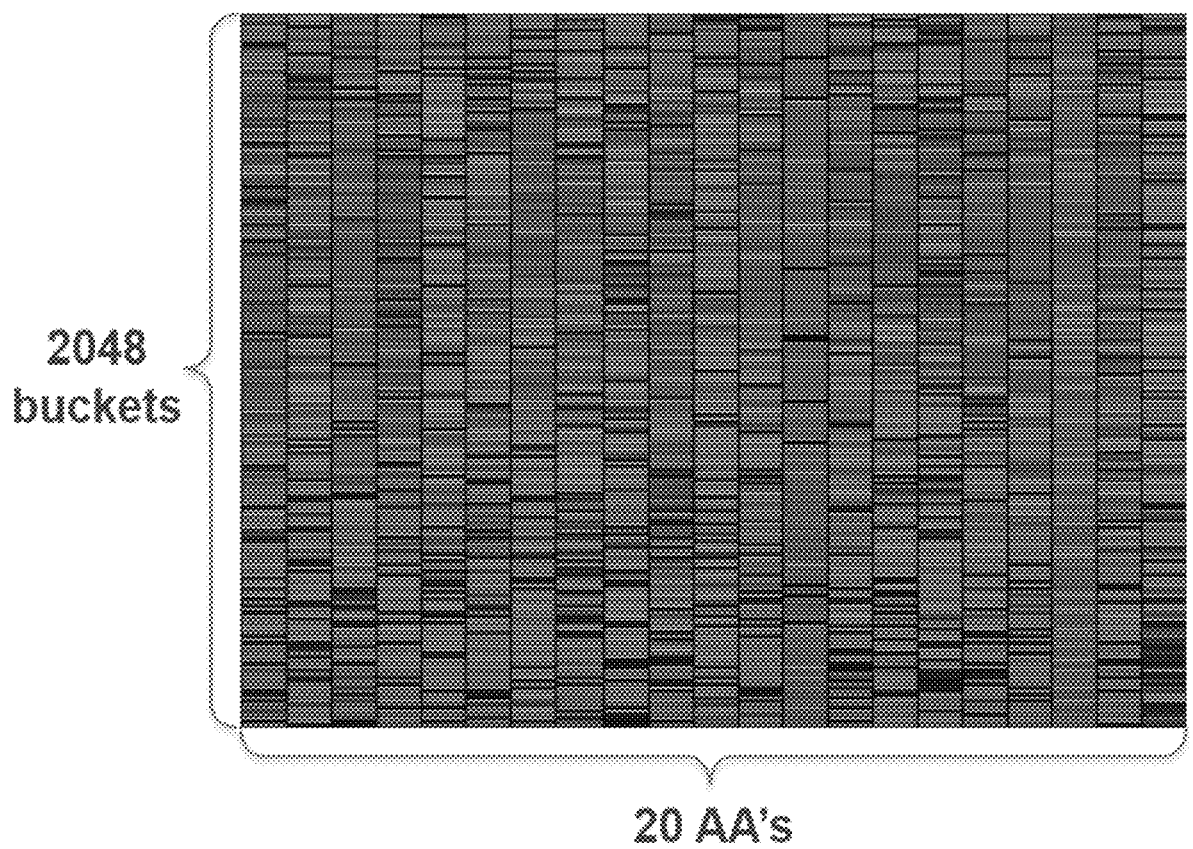

FIG. 11 shows various CNN algorithms using the subsequences as described above. The CNN may look at multiple features using various algorithms The possible features include peptide length, amino acid frequency, amino acid diversity, aliphatic, aromatic, hydrophobic, hydrophilic, positive charge, negative charge and the presence and frequency of the subsequences. FIG. 12C shows an example of image weights from the final layer of a CNN after training.

The CNN training models described above may be combined to determine a short list of possible proteins that could match the sample. A short list of possible proteins is an easier, less time/resource-intensive search than if the list of possible proteins had not been narrowed by the CNN.

The methods and algorithms disclosed herein achieved identification of molecules from mass spectral data. These the methods and algorithms may be applied to confirm the identity of known (spectral matched) molecule or to identify or further characterize unknown spectra such as peptides, cyclic peptides, non-canonical amino acid, known and unknown post-translational modifications, glycans, lipids, fusion peptides, or other variants not found in canonical databases.

In various embodiments, the methods and algorithms disclosed herein may provide additional confidence in the identification of peptides or small molecules, by providing, for instance, amino acid position, number of amino acids, length, type of amino acids, diversity and other information to further interpret mass spectra data. A combination of various models may help triangulate valuable information such as peptide sequence or modifications, or further identify molecular features (glycans, lipids, etc.).

The application of the methods and algorithms disclosed herein may be employed in the characterization of major histocompatibility complex class I (MHC-I) or MCH class II (MHC-II) peptides or confirmation/validation of putative hits (or other peptidome use).

The application of the methods and algorithms disclosed herein may provide a supplemental or alternative approach to existing mass spectrometry search engines (peptide/protein/small molecules) and/or de novo sequencing.

The application of the methods and algorithms disclosed herein may be employed in point of care (POC) devices or instrument control software to provide real-time assessment of spectra to improve decision making.

The methods and algorithms disclosed herein may reduce processing time to identify a protein or other molecule based on its spectra. The methods and algorithms disclosed herein may be used to dynamically tune the CNN in real-time.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth.

What is claimed is:

1. A method of identifying features in mass spectral data, comprising:
   identifying a first mass spectrum matched to an amino acid sequence;
   pooling the amino acid sequence from the first mass spectrum into a plurality of groups of sequential amino acids;
   classifying each amino acid as aliphatic or aromatic and assigning a first feature to each amino acid based on a classification as aliphatic or aromatic;
   classifying each amino acid as hydrophobic or hydrophilic and assigning a second feature to each amino acid based on a classification as hydrophobic or hydrophilic;
   classifying each amino acid as positively charged or negatively charged and assigning a third feature to each amino acid based on a classification as positively charged or negatively charged;
   producing a subsequence for each of the groups of sequential amino acids based on the first feature, the second feature, and the third feature for each amino acid;
   training a convolutional neural network by inputting into the convolutional neural network the subsequence for each of the groups of sequential amino acids to produce a trained convolutional neural network;
   obtaining from a mass spectrometer a second mass spectrum of a protein sample having an unknown amino acid sequence;
   inputting the second mass spectrum into the trained convolutional neural network;
   identifying, by the trained convolutional neural network, a presence or absence of each subsequence in the second mass spectrum of the protein sample; and
   determining, by an output of the trained convolutional neural network, a predicted amino acid sequence corresponding to the second mass spectrum based on the presence or absence of each subsequence.

2. The method of claim 1, further comprising determining, by the output of the trained convolutional neural network, the predicted amino acid sequence based on a frequency of each subsequence.

3. The method of claim 1, further comprising, prior to inputting the first mass spectrum into the convolutional neural network, discretizing the first mass spectrum into a first weighted vector, wherein the first weighted vector corresponds to a peak height in segments of the first mass spectrum.

4. The method of claim 1, wherein the weighted vector corresponds to a peak height in segments of the second mass spectrum.

5. A method of identifying features in mass spectral data, comprising:
   training a convolutional neural network by inputting a mass spectra from a known protein sample and a corresponding known amino acid sequence into the convolutional neural network to produce a trained convolutional neural network;
   obtaining a mass spectra of an unknown protein sample;
   inputting the mass spectra of the unknown protein sample into the trained convolutional neural network;
   determining, by a first output of the trained convolutional neural network, a presence or absence of an amino acid in the unknown protein sample;
   determining, by a second output of the trained convolutional neural network, a length of a peptide sequence of the unknown protein sample; and
   determining, by a third output of the trained convolutional neural network, a frequency of the amino acid in the peptide sequence of the unknown protein sample.

6. The method of claim 5, further comprising discretizing the mass spectra of the unknown protein sample into a one-dimensional vector prior to inputting the mass spectra of the unknown protein sample into the trained convolutional neural network.

7. The method of claim 6, wherein the one-dimensional vector corresponds to a presence or absence of a peak in each segment of the mass spectra of the unknown protein sample.

8. The method of claim 5, further comprising, prior to inputting the mass spectra from the known protein sample into the convolutional neural network, discretizing the mass spectra of the known protein sample into a one-dimensional vector, wherein the one-dimensional vector corresponds to a presence or absence of a peak in each segment of the mass spectra of the known protein sample.

9. The method of claim 5, further comprising, prior to inputting the mass spectra from the known protein sample into the convolutional neural network, discretizing the mass spectra of the known protein sample into a weighted vector, wherein the weighted vector corresponds to a peak height in each segment of the mass spectra of the known protein sample.

10. A method of identifying features in mass spectral data, comprising:
   obtaining a first mass spectra matched to a first amino acid sequence;
   discretizing the first mass spectra by assigning a first binary vector, wherein the first binary vector corresponds to a peak height relative to a threshold in segments of the first mass spectra;
   training a convolutional neural network by inputting the first binary vector and first amino acid sequence into the convolutional neural network to produce a trained convolutional neural network;
   obtaining from a mass spectrometer a second mass spectra from a protein sample having an unknown amino acid sequence;
   discretizing the second mass spectra by assigning a second binary vector, wherein the second binary vector corresponds to a peak height relative to the threshold in segments of the second mass spectra;
   inputting the second binary vector into the trained convolutional neural network; and
   determining, by an output of the trained convolutional neural network, a predicted amino acid sequence for the protein sample.

11. The method of claim 10, further comprising determining, by the output of the trained convolutional neural network, a length of a peptide sequence of the protein sample.

12. The method of claim 10, further comprising training the convolutional neural network by inputting a set of synthetic mass spectra data and corresponding synthetic amino acid sequences into the convolutional neural network.

* * * * *